US008631793B2

(12) United States Patent
Omura et al.

(10) Patent No.: US 8,631,793 B2
(45) Date of Patent: Jan. 21, 2014

(54) NASAL RESPIRATORY MASK SYSTEM AND CONNECTION/DISCONNECTION MEANS USED THEREIN

(75) Inventors: Keiko Omura, Tokyo (JP); Masahide Takishita, Tokyo (JP); Tongoh Chin, Tokyo (JP); Hideharu Shimura, Osaka (JP); Shinya Fujimoto, Osaka (JP); Kazuaki Fujiura, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 651 days.

(21) Appl. No.: 12/225,680

(22) PCT Filed: Mar. 29, 2007

(86) PCT No.: PCT/JP2007/057626
§ 371 (c)(1),
(2), (4) Date: Sep. 26, 2008

(87) PCT Pub. No.: WO2007/114492
PCT Pub. Date: Oct. 11, 2007

(65) Prior Publication Data
US 2009/0173343 A1 Jul. 9, 2009

(30) Foreign Application Priority Data
Mar. 29, 2006 (JP) ................................. 2006-090478

(51) Int. Cl.
*A61M 16/06* (2006.01)
*A62B 18/02* (2006.01)
*A62B 18/08* (2006.01)

(52) U.S. Cl.
USPC ............ 128/207.11; 128/202.27; 128/205.25; 128/206.21

(58) Field of Classification Search
USPC .......... 128/202.27, 207.11, 206.21; 24/591.1, 24/623, 606, 421
See application file for complete search history.

(56) References Cited

U.S. PATENT DOCUMENTS

| 5,146,657 A | * | 9/1992 | Frano | 24/265 H |
| 5,274,887 A | * | 1/1994 | Fudaki | 24/265 H |

(Continued)

FOREIGN PATENT DOCUMENTS

| JP | 44-2489 Y1 | 1/1969 |
| JP | 05-018309 U | 1/1993 |

(Continued)

OTHER PUBLICATIONS

Machine Translation of JP 2000262305 A published Sep. 2000.*

(Continued)

*Primary Examiner* — Justine Yu
*Assistant Examiner* — Valerie L Skorupa
(74) *Attorney, Agent, or Firm* — Rader, Fishman & Grauer PLLC

(57) ABSTRACT

The present invention relates to a nasal respiratory mask system comprising: a nasal mask that is tightly attached to the face of a user and serves as means for leading positive-pressure breathing gas to the nose of the user, a frame to keep the nasal mask at a predetermined position, and a headgear that is mounted on the head in order to attach the nasal mask tightly to the face; wherein, the headgear comprises, on the tip thereof, a headgear strap for adjusting the length of the headgear, the headgear strap comprises a headgear fastener that serves as means for connection/disconnection with the frame, the frame comprises a fastener catch that engages with the headgear fastener, and the fastener catch comprises an axisymmetric guide whose (rotation) axis is the insertion direction of the headgear fastener. The present invention provides a nasal respiratory mask system with which a headgear can be easily connected at the beginning of wearing, twisting of the headgear during wearing is prevented, and disassembly upon daily washing is easy.

15 Claims, 7 Drawing Sheets

(56) References Cited

U.S. PATENT DOCUMENTS

| 6,088,839 A | * | 7/2000 | Utamaru | 2/340 |
| 2009/0145429 A1 | * | 6/2009 | Ging et al. | 128/202.27 |

FOREIGN PATENT DOCUMENTS

| JP | 2000-262305 A | 9/2000 |
| JP | 2004-000572 A | 1/2004 |
| JP | 2005-537903 A | 12/2005 |
| JP | 2006-507858 A | 3/2006 |
| TW | 385640 U | 3/2000 |
| WO | WO2004/014454 A | 2/2004 |
| WO | WO2004/022144 A | 3/2004 |
| WO | WO 2004030736 A1 * | 4/2004 |

OTHER PUBLICATIONS

International Search Report mailed Jun. 19, 2007.
International Preliminary Examination Report mailed Jan. 15, 2008.
Office Action issued in Taiwanese Patent Application No. 096111067, dated Aug. 29, 2012.

* cited by examiner

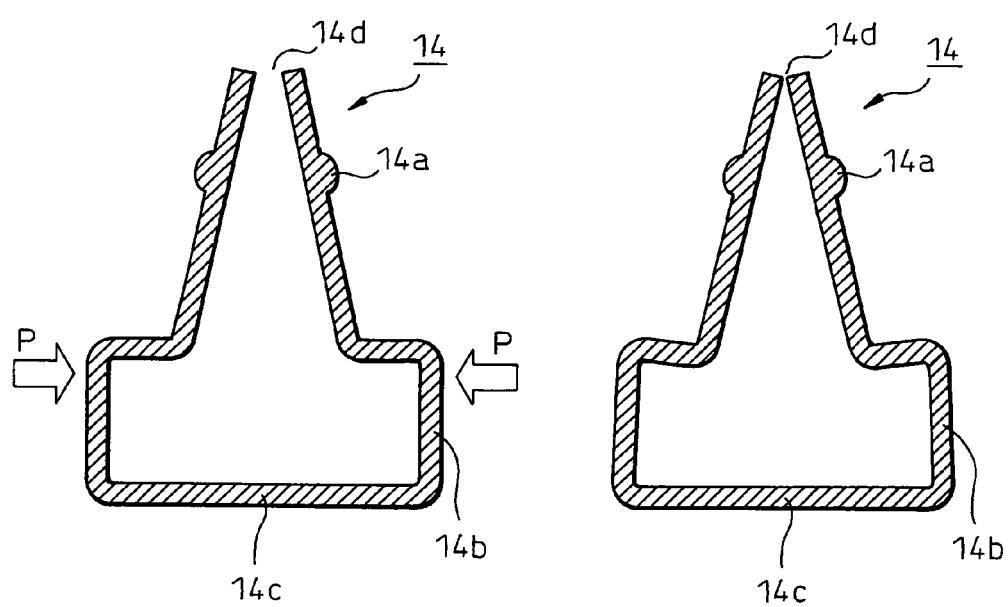

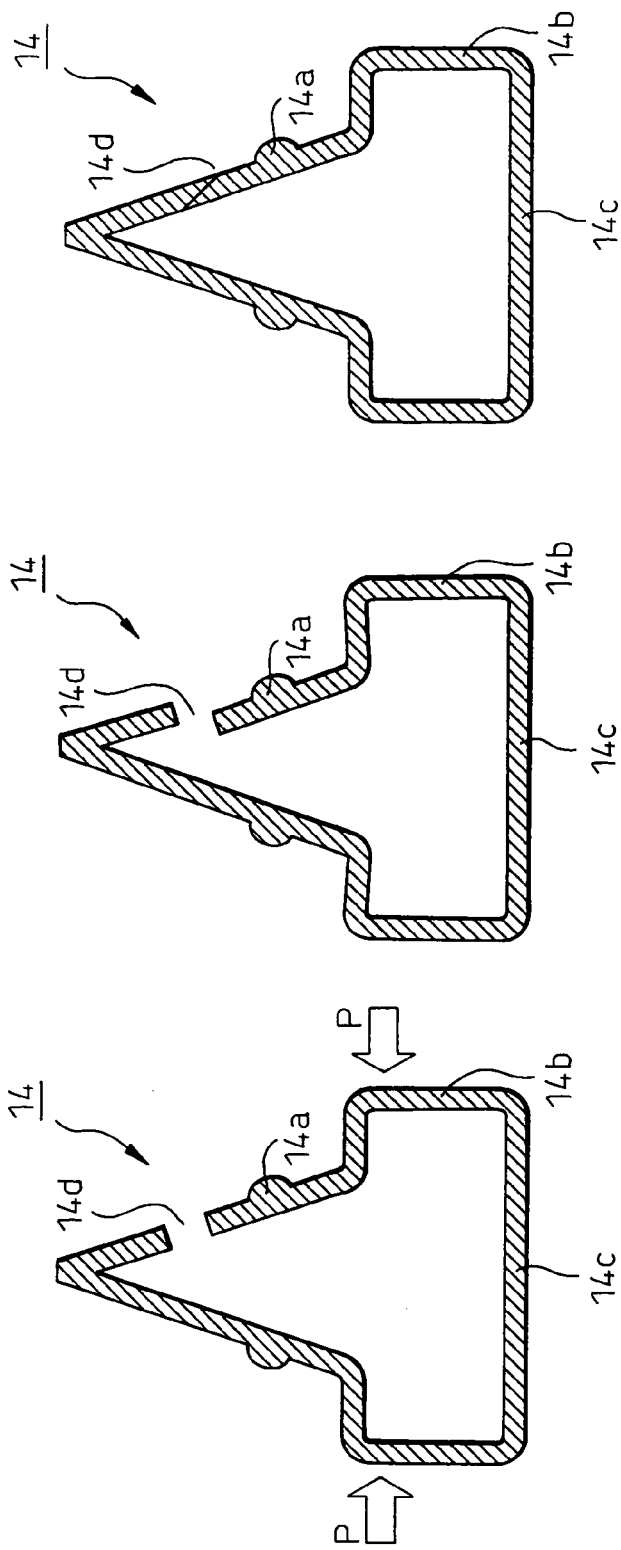

NASAL RESPIRATORY MASK SYSTEM AND CONNECTION/DISCONNECTION MEANS USED THEREIN

TECHNICAL FIELD

The present invention relates to a nasal respiratory mask system used for continuous positive airway pressure (CPAP) therapy suitable for the treatment of sleep apnea syndrome, nasal intermittent positive pressure ventilation (NIPPV) therapy suitable for ventilatory insufficiency, and the like, and to a connection/disconnection means able to be preferably used with this nasal respiratory mask system.

BACKGROUND ART

One of the most effective therapies for sleep apnea syndrome is nasal continuous positive airway pressure (CPAP) therapy, which adopts respiratory equipment that supplies gas at about 400 to about 2000 Pa positive pressure to the nasal cavity of a user during sleeping. In addition, one of the most effective therapies for ventilatory insufficiency is nasal intermittent positive pressure ventilation (NIPPV) therapy, which adopts respiratory equipment that intermittently supplies gas at about 400 to about 2400 Pa positive pressure to the nasal cavity of a user.

In cases of performing therapy using such equipment, in order to persistently supply positive-pressure gas to the nasal cavity of a user, there is used a nasal mask system composed of a hose to lead positive-pressure gas, a nasal respiratory mask, a frame to hold the nasal respiratory mask at a predetermined position, and a headgear to attach the nasal respiratory mask tightly to the face. The headgear comprises a headgear strap with an adjustable length and is connected to the frame through the headgear strap. The headgear strap makes it possible to adjust the tightness of contact between the nasal mask system and the face so that leakage of the positive-pressure gas can be almost eliminated without causing pain. Common means for keeping the length as it is include Velcro (registered trademark), a belt buckle, and the like. Generally, the nasal mask system is not worn when treatment is not administered. When the nasal mask system is taken off, the headgear strap is drawn out from the mask system. Accordingly, the length must be adjusted every time the mask is worn. In a common-nasal mask system, in order to compensate for this disadvantage, the length adjustment function is separated from the connection function to a frame in such a way that the headgear strap is connected to a fastener, the frame is provided with a fastener catch, and the fastener and the fastener catch share the function of connection/disconnection between the headgear and the frame. This nasal mask system dispenses with need for adjustment of the length upon re-wearing of the system.

Regarding methods for the connection between the headgear and the frame in these nasal mask systems, there have been disclosed various nasal mask systems adopting general technology and specific technology since operations for the connection are required to be performed nearby the nose in many cases.

For example, Patent Document 1 proposes a nasal respiratory mask system in which insertion of a fastener is aided by sliding the fastener in an in-plane direction on a guide plane of a fastener catch provided to a frame, and Patent Document 2 proposes a nasal mask system comprising a rotation mechanism to eliminate torsion of a headgear. These nasal respiratory mask systems are effective to some extent for improving operability upon wearing.

However, in these nasal respiratory mask systems, connection of a fastener may sometimes fail when the fastener is going to be inserted in a fastener catch while deviated in a rotating direction around the axis of the direction of insertion.

In addition, for correcting torsion of a headgear after wearing, a fastener must be composed of two or more parts, causing concern over an increase in total weight of the nasal mask system. In addition, there is also concern that the torsion might be still retained if the degree of freedom of rotation is 180 degrees or more in both directions.

Moreover, the headgear is usually washed on a daily basis and resin parts such as a fastener are disconnected at the time of washing. Since these parts are disconnected from a headgear strap portion at that time, the length must be adjusted every time after washing and it becomes difficult to readily attain a stable wearing condition. In addition, since the headgear strap generally has a structure in which the length is adjusted with Velcro (registered trademark) or the like, more frequent adjustment of the length accelerates deterioration of the headgear strap, significantly reducing the lifetime of the headgear. This problem is more serious for nasal respiratory mask systems lacking a connection/disconnection mechanism using a fastener and a fastener catch.

However, no consideration has been given to these points in existing techniques represented by those described above.

Patent Document 1: Japanese Patent Application Laid-open No. 2005-537903

Patent Document 2: Japanese Patent Laid-open Publication No. 2004-000572

DISCLOSURE OF THE INVENTION

In view of various issues of the conventional art described above, the problems to be solved by the present invention are as described below.

An object of the present invention is to provide a nasal respiratory mask system that solves at least one of the problems including, for example, that a headgear can be connected extremely easily upon wearing, that an unpleasant feeling due to torsion of a headgear during wearing is minimized, and that the need to adjust the length of a headgear strap after washing is eliminated.

The present invention relates to a nasal respiratory mask system that is tightly attached to the face of a user, fixed on the head of the user with a headgear, and used for supplying positive-pressure breathing gas to the nose of the user. The nasal respiratory mask system at least comprises a nasal mask that is tightly attached to the face of a user and serves as means for leading positive-pressure breathing gas to the nose of the user, a frame to keep the nasal mask at a predetermined position, and a headgear that is mounted on the head in order to attach the nasal mask tightly to the face, wherein the headgear comprises, on the tip thereof, a headgear strap for adjusting length of said headgear, the headgear strap comprises, on the tip thereof, a headgear fastener that serves as means for connection/disconnection with the frame, the frame comprises a fastener catch that is engaged with the headgear fastener, and the fastener catch comprises an axisymmetric guide whose (rotation) axis is the insertion direction of the headgear fastener.

In addition, the present invention relates to a connection/disconnection means composed of a fastener and a fastener catch, wherein the fastener comprises a pair of laterally symmetrical clamping portions and a tip portion that connects to the front ends of the pair of clamping portions and engages with the fastener catch by being received therein, and the fastener catch comprises an axisymmetric guide whose (rotation) axis is the insertion direction of the fastener.

Moreover, the present invention relates to a connection/disconnection means composed of a strap and a fastener, wherein the strap comprises a tip portion that forms a ring, the fastener comprises a pair of laterally symmetrical clamping portions, a tip portion formed by connecting to the front ends of the pair of clamping portions, and a connecting portion connecting with the strap by being formed extending to each inside from the rear ends of the clamping portions, and the connecting portion has a notch in a portion thereof.

BRIEF DESCRIPTION OF THE DRAWINGS

FIG. 10a illustrates a variation of a headgear fastener, and FIG. 10b illustrates the state in which a headgear fastener is removed from a fastener catch by pressing on a pressing portion of this variation of a headgear fastener.

FIG. 11a illustrates a different variation of a headgear fastener, FIG. 11b illustrates the state in which a headgear fastener is removed from a fastener catch by pressing on a pressing portion of this variation of a headgear fastener, and FIG. 11c illustrates an example of forming a notch in the form of a diagonal slit.

BEST MODE FOR CARRYING OUT THE INVENTION

Figure 1:
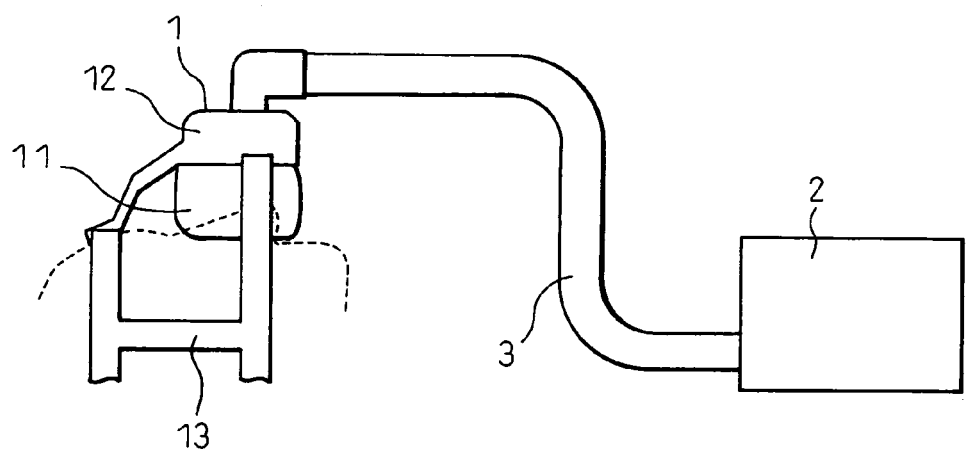
FIG. 1 illustrates the constitution of a common nasal respiratory mask system.

The following provides a more detailed explanation of specific examples of the present invention with reference to the drawings.

The present invention relates to a nasal respiratory mask system comprising a nasal mask that is tightly attached to the face of a user and serves as means for leading positive-pressure breathing gas to the nose of the user, a frame to keep the nasal mask at a predetermined position, and a headgear that is mounted on the head in order to attach the nasal mask tightly to the face, wherein the headgear comprises a headgear strap for adjusting the length of the headgear, the headgear strap comprises, on the tip thereof, a headgear fastener that serves as means for connection/disconnection with the frame, the frame comprises a fastener catch that is engaged with the headgear fastener, and the fastener catch comprises an axisymmetric guide whose (rotation) axis is the direction of inserting the headgear fastener.

The frame used for the nasal respiratory mask system of the present invention is, for example, approximately triangular, and used in such a manner that the basal part of the triangle is placed on the side of both cheeks of a user and the apex of the triangle is placed on the forehead side of the user.

The headgear strap refers to a ribbon portion (13a) attached to the headgear for adjusting the length of headgear. The headgear strap and the headgear may be manufactured separately and combined together for use. A user can adjust the length of the headgear strap as appropriate, for example, by attaching a hook-loop material (so-called Magic Tape (registered trademark)) such as Velcro (registered trademark) (13b) to one surface of the headgear strap. Buckles and the like may also be used as means for adjusting the length of the headgear strap. The headgear and the headgear strap may be made using permeable and elastic-materials including, for example, circular knitted material (jersey material), rubber (breathable neoprene), and the like.

In the nasal respiratory mask system of the present invention, the headgear fastener comprises a tip portion that is received by and engaged with a fastener catch described below, a pressing portion that is means for connection/disconnection between the headgear fastener and the fastener catch (release lever, 14b), and a portion connecting to the headgear strap (strap hook). In addition, the connecting portion (strap hook) of the headgear fastener may be, for example, in a long-bar shape (14c). In this case, a portion of the headgear strap that contacts with this long bar is referred to as the tip of the headgear strap in the present specification. When the strap hook has a long-bar shape, it is preferred to provide a notch 14d in a portion of the strap hook because it enables connection and disconnection between the headgear fastener and the headgear strap without changing the length of the headgear strap. It is also preferred to manufacture the headgear fastener with an elastic resin such as polypropylene or polyacetal for the purpose of reducing weight and imparting elasticity to the headgear fastener.

In the nasal respiratory mask system of the present invention, fastener catches are provided on both ends of the basal part of frame in such a manner that their receptacles for receiving the headgear fasteners are opened to the cheek sides of a user. Since the headgear strap is accordingly under the highest tension when the headgear fastener is engaged with the fastener catch, once the length of the headgear strap is adjusted, the length of headgear strap need not be adjusted after wearing upon subsequent wearing. In addition, when each fastener catch is provided with its receptacle opened slightly downward to the cheek side of a user, the user can wear the mask more easily. The fastener catches may be manufactured with polycarbonate, polyacetal, or the like. When the fastener catches are integrally molded with the frame into a single piece, polycarbonate is preferably used.

In the nasal respiratory mask system of the present invention, the fastener catch comprises an axisymmetric guide whose (rotation) axis is the insertion direction of the headgear fastener. The guide refers to a structure that helps engagement of the headgear fastener and the fastener catch so that the engagement can be carried out only by bringing the headgear fastener close to the fastener catch without strictly adjusting the engagement thereof. As such a structure, there may be mentioned a structure in which the fastener catch has an axisymmetric shape whose (rotation) axis is the insertion direction of the headgear fastener and the receptacle of the fastener catch is wider than the inner receiving part of the fastener catch. According to such a nasal respiratory mask system, even when the headgear fastener is inserted into the fastener catch while the insertion direction of the headgear fastener deviates within the plane perpendicular to insertion direction N or deviates in a rotation direction about the axis of insertion direction N, the headgear fastener can be easily engaged with the fastener catch. Although specific examples of this structure include, for example, a spindle-shaped structure and a conical structure, the structure is not limited to these provided it can demonstrate the above effect.

In the nasal respiratory mask system of the present invention, the headgear fastener has a shape such that it is engaged with the fastener catch having the guide. The headgear fastener is preferably rotatable about the axis of insertion direction N at the engagement site between the headgear fastener and the fastener catch even in the engaged state. According to such a nasal respiratory mask system, a user can correct torsion of the headgear or the headgear strap while wearing the mask system, thereby preventing any unpleasant feeling due to torsion.

In addition, the headgear fastener is rotatable by preferably at least 30 degrees or more, more preferably not less than 30 degrees and less than 180 degrees, and even more preferably not less than 30 degrees and less than 90 degrees at the engagement site between the headgear fastener and the fastener catch. The angle by which the headgear fastener is rotatable is also referred to as allowable rotation angle $\theta$ in the present specification. If the headgear fastener is rotatable by an angle not less than 30 degrees and less than 180 degrees, torsion of the headgear or the headgear strap at the time of wearing can be corrected. Moreover, as far as the headgear fastener remains engaged with the headgear catch after wearing, even if the headgear is twisted in the rotation direction about the axis of insertion direction N due to body movement of a user, since the engagement is constrained within the allowable rotation angle $\theta$, it allows rotation of the headgear fastener to absorb the force between the headgear or the headgear strap and the frame generated by the body movement, and such constraint can also prevent the headgear or the headgear strap from retaining torsion.

The rotatable engagement site can be realized, for example, by providing the headgear fastener with a lock hook 14a, providing the fastener catch with a lock hole 15a that is engaged with the lock hook 14a, and making the shape of lock hole 15a concave along an arc depicted in a plane perpendicular to the insertion direction N of the headgear fastener.

In addition, the present invention also relates to a nasal respiratory mask system comprising a nasal mask that is tightly attached to the face of a user and serves as means for leading positive-pressure breathing gas to the nose of the user, a frame to keep the nasal mask at a predetermined position, and a headgear that is mounted on the head in order to attach the nasal mask tightly to the face, wherein the headgear comprises, on the tip thereof, a headgear strap for adjusting the length of the headgear, the headgear strap comprises, on the tip thereof, a headgear fastener that serves as means for connection/disconnection with the frame, the frame comprises a fastener catch that is engaged with the headgear fastener, the headgear fastener comprises a strap hook that enables connection/disconnection with the headgear strap, and the strap hook comprises a notch in a part thereof and employs a structure capable of elastically deforming the fastener due to the presence of the notch.

In addition, the headgear fastener preferably employs a constitution that allows connection/disconnection of the headgear fastener and the frame by elastically deforming the strap hook. According to such a nasal respiratory mask, the headgear fastener and frame connection/disconnection means and the headgear fastener and headgear strap connection/disconnection means can be integrally composed, thereby making it possible to realize reduced weight of the entire nasal respiratory mask system.

EXAMPLES

First, FIGS. 1 to 4 show the constitutions of common nasal respiratory mask systems during use.

Figure 2:
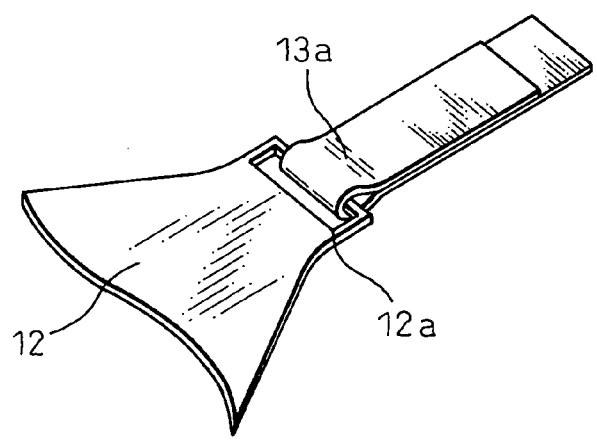
FIG. 2 illustrates direct connection between a headgear 13 and a frame 12 in a common nasal respiratory mask system.

In FIG. 1, a nasal mask 11 made of a soft material such as silicon rubber is kept at an appropriate position by a frame 12 for mounting a nasal mask 11 and a headgear 13 for fixing the frame 12 by utilizing the shape of the head. The nasal mask 11 is used by connecting with respiratory equipment 2 that generates positive-pressure gas and a hose 3 that leads the positive-pressure gas generated by the respiratory equipment 2 to the frame. The frame 12 has an approximately triangular shape and is used in such a manner that the basal part of the triangle is placed on the side of both cheeks of a user and the apex of triangle is placed on the forehead side of the user. The frame 12 and the headgear 13 are fastened together at each apex of the frame. Fixation between the frame and the headgear at the both sides of basal part is generally achieved by putting the headgear strap through the strap hook 12a directly provided on the frame 12 as shown in FIG. 2, or by fixing via a headgear fastener 14 and a fastener catch 15 to achieve easier connection/disconnection (See FIGS. 3 and 4).

Figure 3:
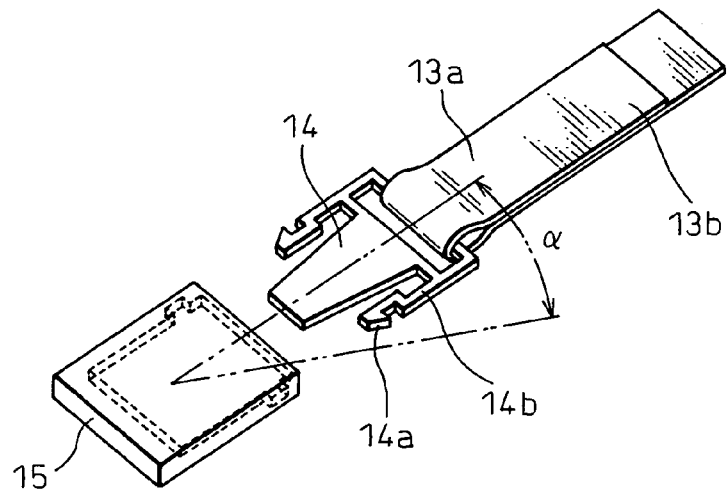
FIG. 3 illustrates the structure of a headgear fastener 14 and a fastener catch 15 in a common nasal respiratory mask system.
Figure 4:
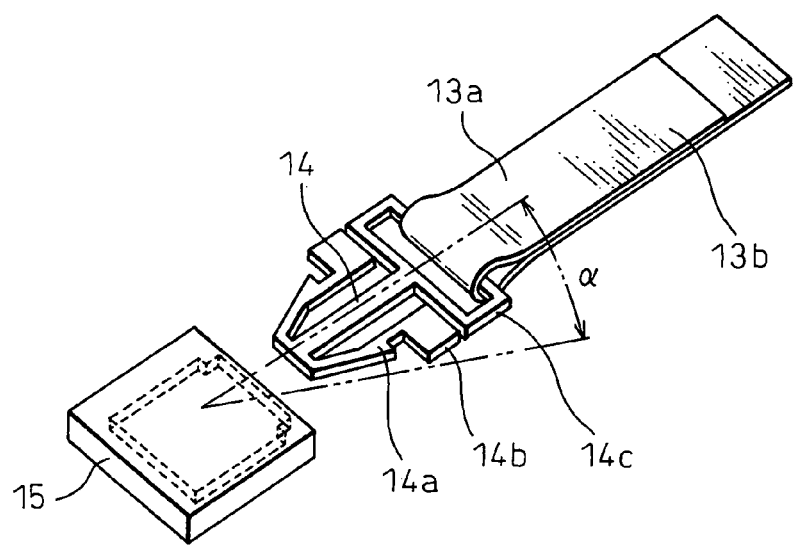
FIG. 4 illustrates the structure of a headgear fastener 14 and a fastener catch 15 in a common nasal respiratory mask system.

Continuing, FIGS. 3 and 4 show common structures used for the headgear fastener 14 and the fastener catch 15. With these structures, the headgear fastener 14 is inserted into the fastener catch 15 and connected using a lock hook 14a, and the headgear fastener 14 can be released from the fastener catch 15 by pinching a release lever 14b with the fingers to release the lock hook 14a. In this case, a deviation in relative positional relationship between the headgear fastener 14 and the fastener catch 15 upon connection can be allowed only for the direction defined by an in-plane error angle in the insertion plane, $\alpha$. In both structures, since an adjustment portion 13b of the headgear strap 13a is disconnected to separate the frame 12 from the headgear 13 or the headgear fastener 14 from the headgear 13 upon washing, it is essential to adjust the length of headgear strap 13a upon re-wearing.

Figure 5:
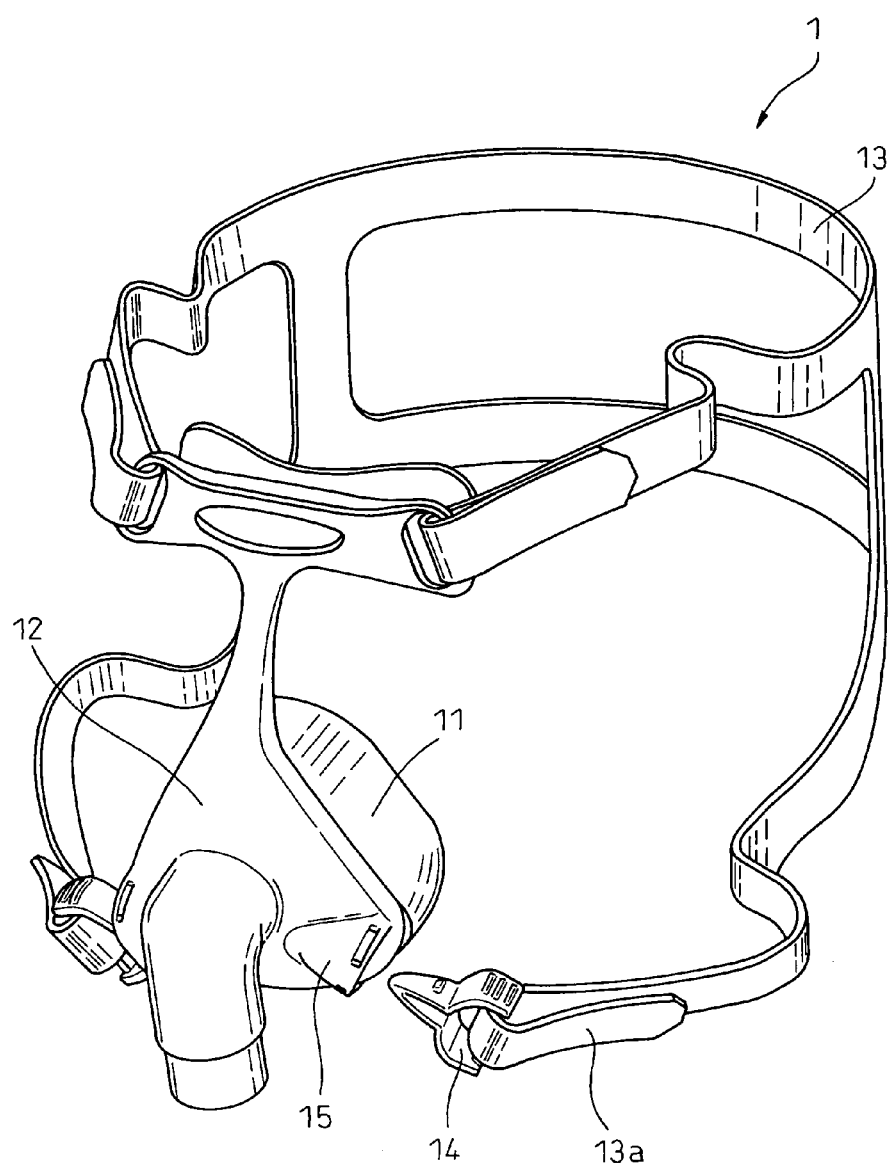
FIG. 5 illustrates the nasal respiratory mask system of the present invention.

FIG. 5 shows a nasal respiratory mask system 1 of the present invention. The nasal respiratory mask system 1 of the present invention comprises a nasal mask 11 that is tightly attached to the face of a user and serves as means for leading positive-pressure breathing gas to the nose of the user, a frame 12 to keep the nasal mask 11 at a predetermined position, and a headgear 13 that is mounted on the head in order to attach the nasal mask tightly to the face. The nasal mask 11 is set between the frame 12 and the user and used while connected to the frame 12 as shown in FIG. 5. The frame 12 has an approximately triangular shape and is used in such a manner that the basal part of triangle is placed on the side of both cheeks of a user and the apex of triangle is placed on the forehead side of the user. As shown in FIG. 5, the frame 12 has a total of four portions connecting to the headgear 13, two on the forehead side and two on the basal part (one for each end). In addition, in the nasal respiratory mask system 1 of the present invention, the frame 12 comprises fastener catches 15 on both ends of the basal part.

Moreover, in the nasal respiratory mask system 1 of the present invention, the headgear 13 has a headgear strap 13a for adjusting the length thereof, and the headgear strap 13a has, on its tip, a headgear fastener 14 that is integrally molded from resin and the like and serves as means for connection/disconnection with the frame 12.

Figure 6:
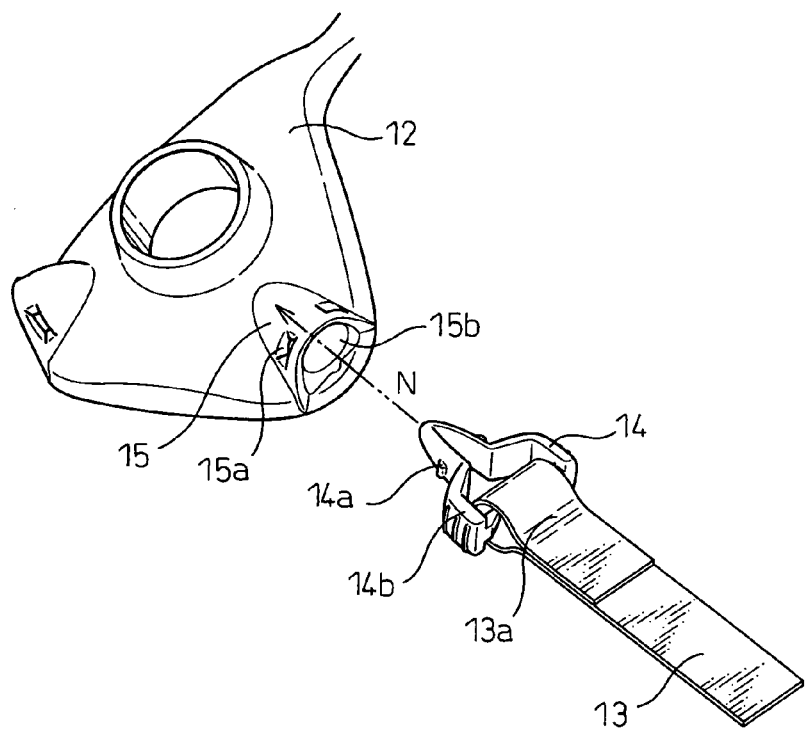
FIG. 6 illustrates a headgear fastener 14 and a fastener catch in the nasal respiratory mask system of the present invention.

A characteristic of the nasal respiratory mask system of the present invention lies in the providing of the fastener catch 15 to the frame 12 by comprising an axisymmetric guide with respect to the direction in which the headgear fastener is inserted (insertion direction N) as shown in FIG. 6. The fastener catch 15 is integrally molded from resin and the like as a portion of the frame 12. The following provides an explanation of the characteristic structure of the present invention that allows deviation in the rotation direction about the axis of insertion direction N with reference to FIG. 6. As shown in FIG. 6, since a guide plane 15b of the fastener catch 15 has an axisymmetric shape whose axis is insertion direction N, during insertion of the headgear fastener 14, it can be inserted without any problem even if inserted with deviation in the rotation direction about the axis of insertion direction N. Moreover, deviation within the plane perpendicular to insertion direction N is also tolerable when the guide plane has an indentation having a spindle shape, for example, a cone shape.

Figure 7:
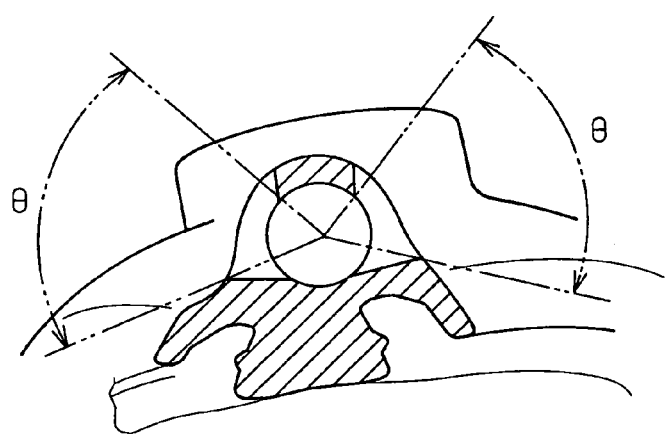
FIG. 7 illustrates rotation of the site where a headgear fastener 14 is engaged with a fastener catch in the nasal respiratory mask system of the present invention.

In addition, when the shape of lock hole 15a, which is directly engaged with the lock hook 14a, is made to be concave extending along an arc depicted in a plane perpendicular to the N axis so that the headgear fastener 14 can rotate by an allowable rotation angle θ during insertion, for example, by not less than 30 and less than 180 degrees (See FIG. 7), the headgear fastener 14 can be engaged with the fastener catch 15 at a predetermined position even if they are mutually deviated in the rotation direction upon insertion. In addition, when the user moves the body, although the headgear 13 or the headgear strap 13a tends to twist in the rotation direction about the axis of insertion direction N, since the lock hook 14a is constrained by the lock hole 15a within the allowable rotation angle θ, the headgear 13 or the headgear strap 13a can be prevented from retaining torsion.

Figure 8:
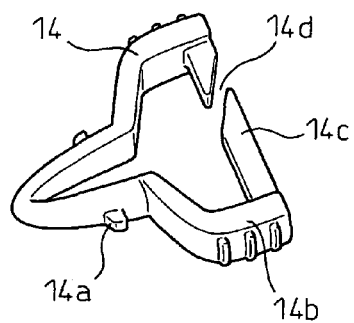
FIG. 8 illustrates a headgear fastener 14 and a strap hook 14c provided on the headgear fastener of the nasal respiratory mask system of the present invention.
Figure 9:
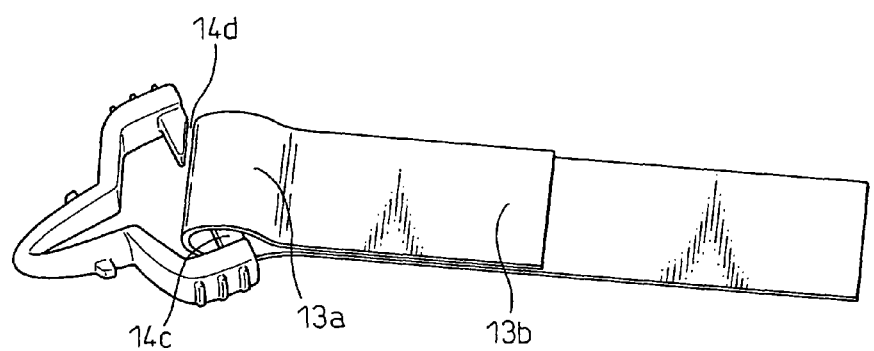
FIG. 9 illustrates connection/disconnection of a headgear strap 13a by a mechanism using a strap hook 14c in the nasal respiratory mask system of the present invention.

In addition, the following provides an explanation of another characteristic of the present invention in the form of the headgear hook 14c with reference to FIG. 8. The strap hook 14c has a notch 14d in a part thereof as shown in FIG. 8. Owing to the presence of the notch 14d in the strap hook 14c, the headgear strap 13a can be disconnected while keeping its pre-adjusted length by passing it through the notch 14d as shown in FIG. 9 when the headgear fastener 14 is removed from the headgear 13 upon washing or the like. The headgear fastener 14 can be re-connected by following the reverse procedure, thereby eliminating the bother of adjusting the fixed position of the headgear strap to re-adjust the length of headgear. Furthermore, when the mask is worn, the presence of notch 14d does not affect the tension of headgear 13 or cause spontaneous disconnection of the headgear strap 13a. Moreover, this notch 14d may be also applied to connection using the strap hook 14a provided directly to the frame 12 without using the headgear fastener 14 and the fastener catch 15.

In addition, the head gear fastener 14 shown in FIG. 8 is provided with a pair of laterally symmetrical release levers 14b, and a pair of lock hooks 14a that form protruding portions coupled approximately in a V-shape to the front end of these pair of release levers 14b, and are located on the outside of this approximately V-shaped front end. In addition, as a result of having a notch 14d in a portion of a strap hook 14c formed extending to the inside respectively from the rear ends of the pair of laterally symmetrical release levers 14b, the entire headgear fastener 14, including the strap hook 14c, has a leaf spring structure bent at the tip of the headgear fastener 14. Consequently, when the headgear fastener 14 is inserted into the fastener catch 15 formed in a concave portion, the pair of lock hooks 14a are able to respectively engage with the pair of lock holes 15a as a result of the headgear fastener 14 elastically deflecting slightly to the inside. In addition, the structure is such that, when the clamping portions in the form of the release levers 14b provided on the headgear fastener 14 are pinched with the fingers, the strap hook 14c is elastically deformed, the lock hooks 14a are released from the lock holes 15a, and the headgear fastener 14 can be removed from the fastener catch 15. In this case, the connection/disconnection means of the headgear fastener 14 and the frame 12 and the connection/disconnection means of the headgear fastener 14 and the headgear strap 13a can be integrally composed making it possible to reduce the weight of the overall nasal respiratory mask system.

In addition, although the headgear fastener 14 shown in FIG. 8 has a notch 14d in a portion of the strap hook 14c serving as a connecting portion with the headgear strap 13a as previously described, this notch 14d is formed on an angle such that the outside opens at a location close to one of the release levers 14b while the inside opens closer to the center. As a result, the structure allows the strap hook 14c to be easily connected and disconnected by passing the headgear strap 13a through the notch 14d. In addition, release levers 14b are provided with a plurality of projections so as to facilitate easy and smooth operation with the fingers and to avoid slipping fingers on release levers 14b.

FIGS. 10a, 10a and FIGS. 11a and 11b depict variations of headgear fastener 14. Although these are similar to the example of FIG. 8 with respect to having a pair of laterally symmetrical release levers 14b, in the variation of FIG. 10a, the approximately V-shaped protruding portion coupled to the front end of these pair of release levers 14b has a notch 14d in the location of the tip thereof. Conversely, there is no notch provided in strap hook 14c serving as the connecting portion with the headgear strap 13a. In this variation, when connecting or disconnecting the headgear strap 13a to and from the headgear fastener 14, the headgear strap 13a is passed through this notch 14d located in the tip thereof. In addition, when the headgear fastener 14 is connected to the frame 12 by inserting into the fastener catch 15, by inserting the tip thereof into this approximately V shape, this portion deflects to the inside due to the elasticity thereof as shown in FIG. 10b, and the pair of lock hooks 14a fit into the pair of look holes 15a of the fastener catch 15 thereby completing connection. In addition, when removing the headgear fastener 14 from the frame 12, by pressing the pair of release levers 14b to the inside in the direction of arrows P, the pair of lock hooks 14a are released from the lock holes 15a of the fastener catch 15, and the headgear fastener can be disconnected from the frame 12.

In the variation of FIG. 11a, an approximately V-shaped protruding portion coupled to the front end of the pair of release levers 14b has a notch 14d at a location between the location of the tip and a lock hook 14a on one side thereof. Similar the aforementioned variation, a notch is not provided in strap hook 14c serving as a connecting portion with the headgear strap 13a. Although this variation is similar to the aforementioned variation in that, when connecting or disconnecting the headgear strap 13a to and from the headgear fastener 14, the headgear strap 13a is passed through the notch, and when connecting the headgear fastener 14 to the frame 12 by inserting into the fastener catch 15, by inserting the tip directly into the approximately V-shaped portion, these portions are deflected to the inside as shown in FIG. 11b due to the elasticity thereof, enabling the pair of lock hooks 14a to fit into the pair of lock holes 15a of the fastener catch 15 thereby resulting in connection, when removing the headgear fastener 14 from the frame 12, by pressing the pair of release levers 14b to the inside in the direction of arrows P, only the lock hook 14a on the side provided with the notch 14d is pulled to the inside due to the elasticity thereof, thereby resulting in both lock hooks 14a being released from the lock holes 15a of the fastener catch 15. In addition, in this variation, when the notch 14d is formed in the form of a diagonal slit as shown in FIG. 11c and headgear strap 13a is connected or disconnected from fastener catch 15, by pressing the pair of release levers at the rear portion of the slit to the inside, notch 14d opens or lock hook 14a is moved to the inside, thereby enabling it to be released from the lock hole 15a.

While preferred embodiments of the present invention have been described and illustrated above, it should be understood that these are exemplary of the present invention and are not to be considered as limiting. Additions, omissions, substitutions and other modifications can be made without departing from the spirit or scope of the present invention.

For example, the following provides an explanation of a constitution that differs from the aforementioned embodiments.

Although the aforementioned explanations of the embodiments described the shape of the headgear fastener 14 as being laterally symmetrical, the shape of the headgear fastener 14 is not limited to that having lateral symmetry, but rather, may also have a shape in which the distance between the pair of lock hooks 14a on the tip of the headgear fastener is slightly reduced, and these lock hooks 14a can be released from the pair of lock holes 15a of the fastener catch 15 when a pair of release levers are pressed to the inside with the fingers. Thus, for example, the tip protruding approximately in a V shape of the headgear fastener 14 that fits into the fastener catch 15 may be provided at a location closer to one of the pair of release levers 14b.

In addition, although the aforementioned explanations of the examples described the frame 12 and the headgear fastener 14 being integrally molded from a resin, these may also be formed with a different material such as metal, or a plurality of parts may be composed in combination. However, the headgear fastener 14 preferably employs a structure that allows lock hooks to be engaged and released to and from lock holes of a fastener catch by imparting with elasticity as a result of having a notch at a single location as previously described.

INDUSTRIAL APPLICABILITY

According to the present invention, a nasal respiratory mask system used in CPAP therapy, NIPPV therapy and the like is provided.

In addition, the present invention has the remarkable effects of enabling the fastener to be connected without concern about deviation in the rotation direction about the axis of insertion direction of the fastener when the fastener is inserted into the fastener catch, and being able to prevent the unpleasant feeling caused by torsion of the headgear after wearing while also realizing a reduction in weight.

Moreover, the present invention also has the remarkable effect of enabling the need for adjustment upon re-wearing to be eliminated and being able to suppress deterioration of the headgear since the headgear can be connected/disconnected without removing the headgear strap when washing the headgear.

The invention claimed is:
1. A nasal respiratory mask system comprising:
a nasal mask configured to be attachable to a face of a user and serves as means for supplying positive-pressure breathing gas to a nose of the user;
a frame to keep the nasal mask at a predetermined position; and
a headgear configured to be mountable on a head of the user in order for the nasal mask to be attachable to the face of the user, wherein
the headgear comprises a headgear strap configured to adjust the length of the headgear, the headgear strap comprises a headgear fastener that serves as means for connection/disconnection with the frame, the frame comprises a fastener catch that engages with the headgear fastener, the fastener catch comprises an axisymmetric guide whose axis is an insertion direction of the headgear fastener, the shape of the guide is an indentation having a spindle shape or a cone shape, and the headgear fastener has an approximately V-shaped protruding portion adapted to the indentation,
wherein, at an open end of the guide, the indentation has a smooth circular inner wall along an entire periphery thereof and extending a predetermined axial length of the indentation such that the headgear fastener can be inserted into the fastener catch in any rotational direction,
wherein the headgear fastener is rotatable about the axis of the direction of insertion even when engaged at the engagement site with the fastener catch and
wherein the headgear fastener is rotatable by at least 30 degrees with respect to the fastener catch at the engagement site with the fastener catch.

2. The nasal respiratory mask system according to claim 1, wherein the headgear fastener is rotatable by at least 30 degrees and less than 180 degrees at the engagement site with the fastener catch.

3. The nasal respiratory mask system according to claim 1, wherein the headgear fastener is provided with a lock hook, the fastener catch is provided with a lock hole that engages with the lock hook, and the lock hole is concave along an arc depicted in a plane perpendicular to the insertion direction of the headgear fastener.

4. The nasal respiratory mask system according to claim 1, wherein the headgear fastener has a means for allowing connection/disconnection of the headgear fastener and the headgear strap without adjusting the length of the headgear strap.

5. The nasal respiratory mask system according to claim 1, wherein the headgear fastener comprises:
a pair of clamping portions,
an approximately V-shaped tip portion that is formed extending from each of front ends of the pair of clamping portions and engages with the fastener catch by being received therein, and
a connecting portion with the headgear strap that is formed extending to the inside from each of the rear ends of the clamping portions; wherein,
the connecting portion and/or the tip portion has a notch in a portion thereof resulting in a structure that allows elastic deformation of the headgear fastener by the notch.

6. The nasal respiratory mask system according to claim 1, wherein during rotation, the headgear fastener is kept to be engaged with the fastener catch.

7. The nasal respiratory mask system according to claim 1, wherein the headgear fastener is not disengaged from the fastener catch even if the headgear fastener is rotated.

8. A connection/disconnection means comprising a fastener and a fastener catch;

the fastener comprises a pair of clamping portions, and an approximately V-shaped tip portion that is formed protruding on front ends of the pair of clamping portions and engages with the fastener catch by being received therein; and the fastener catch comprises an axisymmetric guide whose axis is an insertion direction of the fastener, the shape of the guide is an indentation having a spindle shape or a cone shape, and the fastener has an approximately V-shaped protruding portion adapted to the indentation wherein, at an open end of the guide, the indentation has a smooth circular inner wall along an entire periphery thereof and extending a predetermined axial length of the indentation such that the headgear fastener can be inserted into the fastener catch in any rotational direction, wherein the fastener is rotatable about the axis of the insertion direction even when engaged at an engagement site with the fastener catch and wherein the fastener is rotatable by at least 30 degrees with respect to the fastener catch at the engagement site with the fastener catch.

9. The connection/disconnection means according to claim 8, wherein the fastener is rotatable by at least 30 degrees and less than 180 degrees at the engagement site with the fastener catch.

10. The connection/disconnection means according to claim 8, wherein the fastener is provided with a lock hook on the tip thereof, the fastener catch is provided with a lock hole that engages with the lock hook, and the lock hole is concave along an arc depicted in a plane perpendicular to the insertion direction of the fastener.

11. The connection/disconnection means according to claim 8, wherein the fastener is a headgear fastener, is comprised of a connecting portion serving as a connection/disconnection means with a headgear strap that is formed extending to the inside from each of the rear ends of the clamping portions, the connecting portion and/or the tip portion has a notch in a portion thereof resulting in a structure that allows elastic deformation of the headgear fastener by the notch.

12. The connection/disconnection means according to claim 8, wherein during rotation, the fastener is kept to be engaged with the fastener catch.

13. The connection/disconnection means according to claim 8, wherein the fastener is not disengaged from the fastener catch even if the fastener is rotated.

14. A nasal respiratory mask system comprising:

a nasal mask configured to be attachable to a face of a user and serves as means for supplying positive-pressure breathing gas to a nose of the user;

a frame to keep the nasal mask at a predetermined position; and a headgear configured to be mountable on a head of the user in order for the nasal mask to be attachable to the face of the user, wherein the headgear comprises a headgear strap configured to adjust the length of the headgear, the headgear strap comprises a headgear fastener that serves as means for connection/disconnection with the frame, the frame comprises a fastener catch that engages with the headgear fastener, the fastener catch comprises an axisymmetric guide whose axis is an insertion direction of the headgear fastener, the shape of the guide is an indentation having a spindle shape or a cone shape, and the headgear fastener has an approximately V-shaped protruding portion adapted to the indentation, wherein the headgear fastener includes a lock hook piece, a clamping portion and a strap hook integrally connected together with a notch incorporated with one of the lock hook piece, the clamping portion and the strap hook or disposed between connected ones of the lock hook piece, the clamping portion and the strap hook and wherein, at an open end of the guide, the indentation has a smooth circular inner wall along an entire periphery thereof and extending a predetermined axial length of the indentation such that the headgear fastener can be inserted into the fastener catch in any rotational direction.

15. A nasal respiratory mask system comprising:

a nasal mask configured to be attachable to a face of a user and serves as means for supplying positive-pressure breathing gas to a nose of the user;

a frame to keep the nasal mask at a predetermined position; and a headgear configured to be mountable on a head of the user in order for the nasal mask to be attachable to the face of the user, wherein the headgear includes a headgear strap configured to adjust the length of the headgear, the headgear strap includes a headgear fastener for connection/disconnection with the frame, the frame includes a fastener catch that engages with the headgear fastener, the fastener catch includes a guide body disposed about and extending along an axisymmetric axis defining an insertion/retraction direction of the headgear fastener, the guide body having an inner guide body surface forming a generally conically-shaped reception hole extending along and about the axisymmetric axis and having a pair of lock holes extending through the guide body transversely to the axisymmetric axis and into the conically-shaped reception hole, the headgear fastener including a pair of clamp arms connected together at respective proximal clamp arm ends to form a generally V-shaped configuration and extending therefrom to terminate in respective distal clamp arm ends, each one of the pair of clamp arms having an inner clamp arm surface with respective ones of the inner clamp arm surfaces facing each other and an outer clamp arm surface facing away from the respective inner clamp arm surfaces, a pair of release levers with a respective one of the release levers integrally connected to respective ones of the distal clamp arm ends, a strap hook extending between and integrally connected to at least one of the pair of release levers for retaining the headgear strap to the headgear fastener and a pair of lock hook projections with a respective one of the pair of lock hook projections integrally connected to and projecting outwardly from respective ones of the outer clamp arm surfaces, wherein respective ones of the outer clamp arm surfaces are arcuate in shape as viewed cross-sectionally in a plane extending transversely to the axisymmetric axis such that, when the pair of clamp arms are inserted into the conically-shaped reception hole of the guide body, the outer clamp arm surfaces of the respective ones of the pair of clamp arm members arcuately comport with and facially oppose the inner guide body surface while the pair of lock hook projections are received in respective ones of the pair of lock holes.

* * * * *